United States Patent [19]

Winchel

[11] Patent Number: Plant 7,052

[45] Date of Patent: Oct. 31, 1989

[54] HYBRID TEA ROSE PLANT NAMED BURAM

[75] Inventor: Joseph Winchel, Harbor City, Calif.

[73] Assignee: Larry J. Burks, Tyler, Tex.

[21] Appl. No.: 268,937

[22] Filed: Nov. 7, 1988

[51] Int. Cl.[4] ..... A01H 5/00

[52] U.S. Cl. ..... Plt./21

[58] Field of Search ..... Plt./20, 21

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A new hybrid tea rose variety of bright red coloring and exhibition form.

1 Drawing Sheet

SUMMARY OF THE INVENTION

The present invention relates to a new and distinct variety of rose plant of the hybrid tea rose class, which was originated by my crossing as seed and pollen parents two unnamed, unpatented seedlings of my creation. The varietal denomination of the new cultivar is "Buram".

Among the novel characteristics possessed by this new variety which distinguish it from its parents and all other varieties of which I am aware are flowers of brilliant red color and exhibition form borne singly on a vigorous plant. Asexual reproduction by budding of the new variety as performed in Smith County, Tex., shows that the foregoing and other distinguishing characteristics come true to form and are established and transmitted through succeeding propagations.

The new and improved rose variety which I have developed is an unusually fine hybrid tea rose featuring flowers of strong red coloration and good exhibition form which hold color well through maturity.

BRIEF DESCRIPTION OF DRAWING

The accompanying drawing shows typical specimens of the vegetative growth and flowers of the new variety in different stages of development and depicted in color as nearly true as it is reasonably possible to make the same in a color illustration of this character.

DESCRIPTION OF PREFERRED EMBODIMENT

The following is a detailed description of my new variety, with color terminology in accordance with The Royal Horticultural Society Colour Chart (R.H.S.C.C.). The terminology used in color description herein refers to plate numbers in the aforementioned color chart, e.g., "46A" is plate 46A of The Royal Horticultural Society Colour Chart.

Parentage: Seedling.

*Seed parent.*—Unnamed seedling.

*Pollen parent.*—Unnamed seedling.

Class: Hybrid Tea.

The following observations are made of specimens grown outdoors in Smith County, Tex., during the month of May.

FLOWER

Blooming habit: Recurrent.

A. Bud:

(1) *Size.*—Large.

(2) *Form.*—Ovoid, high centered.

(3) *Color.*—When sepals first divide — near 46A; when petals begin to unfurl — near 46B.

(4) *Sepals.*—Simple, longer than bud.

(5) *Peduncle.*—Length — long. Aspect — straight. Strength — erect, strong. Color — reddish green, near 182A.

B. Bloom:

(1) *Size.*—Average size when fully expanded — about $4\frac{3}{4}$ -inches.

(2) *Borne.*—Singly.

(3) *Form.*—High centered, exhibition type, outer petals quill to points, inner petals roll under.

(4) *Petalage.*—Number of petals under normal conditions — about 30.

(5) *Color.*—After sepals fall and petals unfurl, flower coloring is near 46A to 46B. Petal coloration is substantially uniform and color of inner and outer petals appears uniform. Petaloids, which are few, may have occasional white streaks. Color holds well through maturity.

C. Petals:

(1) *Texture.*—Thick.

(2) *Appearance.*—Inside satiny and outside satiny.

(3) *Form.*—Acuminate.

(4) *Arrangement.*—Imbricated, regularly arranged.

(5) *Petaloids in center.*—Few.

(6) *Persistence.*—Average.

(7) *Fragrance.*—Slight.

(8) *Lasting quality.*—Average to long lasting.

REPRODUCTIVE ORGANS

A. Stamens, filaments and anthers:

(1) *Arrangement.*—Regularly arranged around styles.

(b 2) *Color.*—Orange to orange-red.

B. Pollen:

*Color.*—Yellow.

C. Styles:

*Even.*—Medium.

D. Stigmas:

*Color.*—Cream colored.

E. Hips:

*Shape.*—Globular.

*Size.*—Medium.

*Color.*—Orange yellow; seeds do not protrude.

PLANT

A. Form: Upright.

B. Growth: Vigorous.

*Height attained.*—About 5½ feet.

C. Foliage: Compound 5 to 7 leaflets.

(1) *Size.*—Large.

(2) *Quantity.*—Abundant.

(3) *Color.*—New foliage: purplish green Old foliage: Upper side — near 147A. Under side — near to 147B.

(4) *Shape.*—Ovoid, acuminate.

(5) *Texture.*—Upper side is leathery and under side is dull.

(6) *Edge.*—Serrate.

(7) *Serration.*—Simple.

(8) *Leaf stem.*—Color — light green.

(9) *Stipules.*—Medium.

(10) *Resistance to disease.*—Blackspot — Good. Mildew — Good. Rust — Good.

D. Wood:

(1) *New wood.*—Color — light green with purplish red cast. Bark — smooth.

(2) *Old wood.*—Color — dark green. Bark — smooth.

E. Thorns:

(1) *Thorns.*—Quantity (main stalk) — ordinary. On laterals from stalk — average. Length — medium. Color — tan to greenish brown. Position — regular.

(2) *Prickles.*—Ordinary.

F. Winter hardiness: Average winter hardiness.

I claim:

1. A new and distinct variety of rose plant of the hybrid tea class, substantially as shown and described, characterized particularly by flowers with exhibition form and brilliant red coloration.

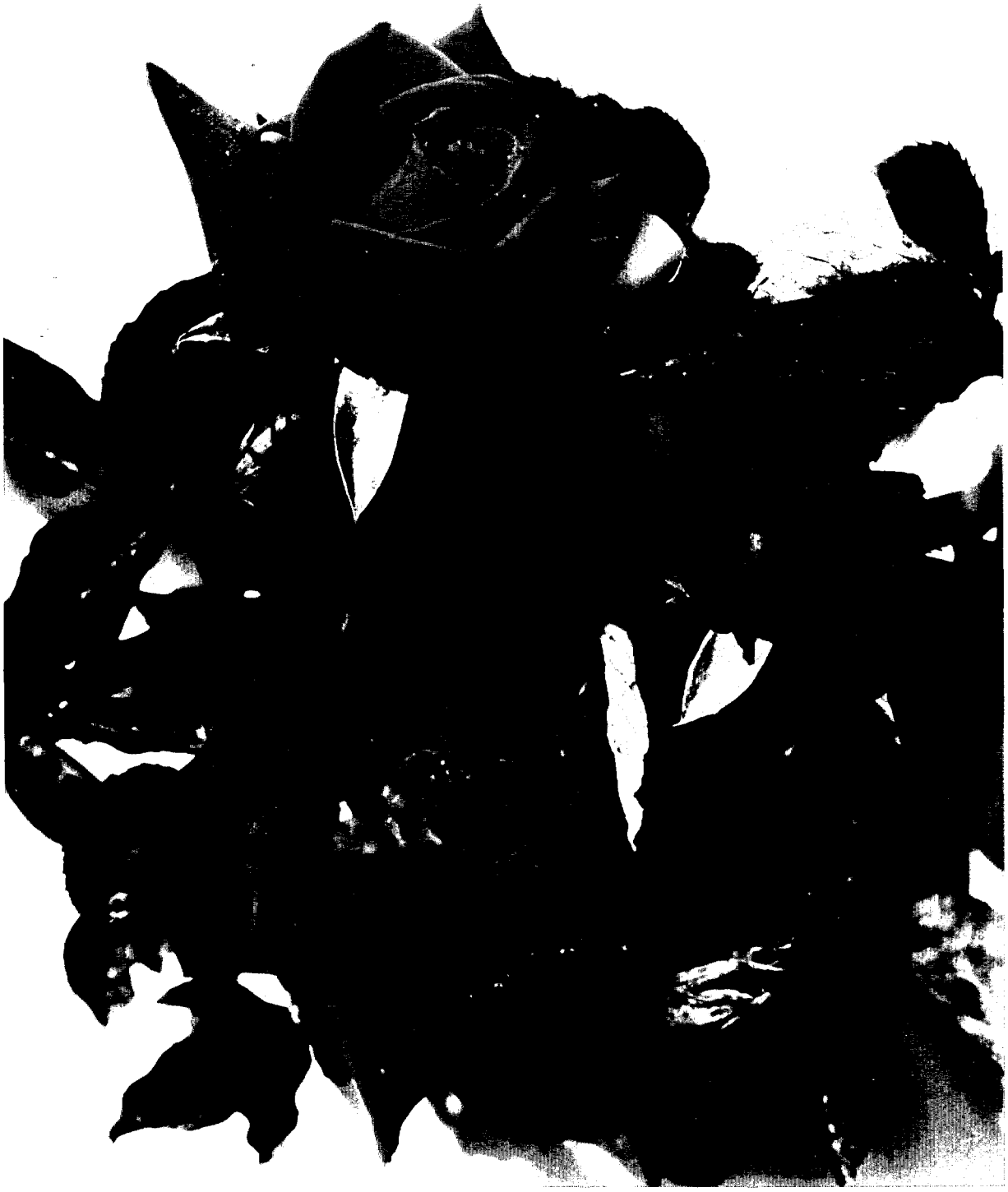

* * * * *